(12) United States Patent
Zeun et al.

(10) Patent No.: US 8,691,727 B2
(45) Date of Patent: Apr. 8, 2014

(54) PESTICIDAL COMPOSITIONS

(75) Inventors: Ronald Zeun, Stein (CH); Clifford George Watrin, Greensboro, NC (US); Michael Oostendorp, Basel (CH); Franz Brandl, Basel (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 1258 days.

(21) Appl. No.: 11/563,240

(22) Filed: Nov. 27, 2006

(65) Prior Publication Data

US 2007/0135506 A1  Jun. 14, 2007

Related U.S. Application Data

(63) Continuation-in-part of application No. PCT/EP2006/004094, filed on May 2, 2006.

(30) Foreign Application Priority Data

May 3, 2005 (GB) .................................. 0508993.3
Nov. 1, 2006 (EP) .................................. 06022767

(51) Int. Cl.
  *A01N 43/00* (2006.01)

(52) U.S. Cl.
  USPC ............ 504/139; 504/118; 504/123; 504/129

(58) Field of Classification Search
  USPC .................................. 504/139, 123, 129, 118
  See application file for complete search history.

(56) References Cited

U.S. PATENT DOCUMENTS

| | | | |
|---|---|---|---|
| 5,215,747 | A | 6/1993 | Hairston et al. |
| 6,767,647 | B2 | 7/2004 | Swofford et al. |

FOREIGN PATENT DOCUMENTS

| | | |
|---|---|---|
| EP | 336489 | 10/1989 |
| EP | 524411 | 1/1993 |
| EP | 539332 | 1/1993 |
| EP | 677246 | 10/1995 |
| EP | 857421 | 8/1998 |
| EP | 1563731 | 8/2005 |
| GB | 2176106 | 12/1986 |
| GB | 2399754 | 9/2004 |
| JP | 54070426 | 6/1979 |
| WO | 9011011 | 10/1990 |
| WO | 0160159 | 8/2001 |
| WO | 0201955 | 1/2002 |
| WO | 02058454 | 8/2002 |
| WO | 03090538 | 11/2003 |
| WO | 2004091294 | 10/2004 |
| WO | 2005094583 | 10/2004 |
| WO | 2004095926 | 11/2004 |
| WO | 2004095929 | 11/2004 |
| WO | 2005077180 | 8/2005 |
| WO | 2005077183 | 8/2005 |
| WO | 2006069701 | 8/2005 |
| WO | 2005110080 | 11/2005 |
| WO | 2005120234 | 12/2005 |
| WO | 2006015728 | 2/2006 |
| WO | 2006015865 | 2/2006 |
| WO | 2006037633 | 4/2006 |
| WO | 2006066873 | 6/2006 |
| WO | 2006659885 | 6/2006 |
| WO | 2006069701 | 7/2006 |
| WO | 2006069716 | 7/2006 |
| WO | 2006100037 | 9/2006 |
| WO | 2006102657 | 9/2006 |
| WO | 2006117192 | 11/2006 |
| WO | 2006134347 | 12/2006 |
| WO | PCT/EP2007/00917 | 10/2007 |
| WO | 0201955 | 5/2008 |
| WO | 2008052681 | 5/2008 |

OTHER PUBLICATIONS

Falloon et al. (Resistance in *Peronospora viciae* to phenylamide fungicides:reduced efficacy of seed treatment of pea (*Pisum sativum*) and assessment of alternatives, Crop Protection, Elsevier Science 2000, vol. 19, pp. 313-325).*
RD292080: "Microbiocidal Combination to Protect Plants;" Anonymous; XP007112861; Research Disclosure, vol. 292, 08, 1988, p. 625.

* cited by examiner

*Primary Examiner* — Rebecca Prouty
*Assistant Examiner* — Danielle Sullivan
(74) *Attorney, Agent, or Firm* — Brian D. McAlhaney

(57) ABSTRACT

A method of controlling or preventing pathogenic damage or pest damage in a plant propagation material, a plant, parts of a plant and/or plant organs that grow at a later point in time, which comprises applying on the plant, part of the plant, or surroundings thereof, a pesticidal combination comprising, for example, at least three active ingredient components optionally together with one or more customary formulation auxiliaries, wherein component (I) is one or more of an -azole fungicide, component (II) is one or more of a phenylamide fungicide, component (III) is one or more of a strobilurin fungicide and/or one or more of a phenylpyrrole fungicide, in any desired sequence or simultaneously.

11 Claims, No Drawings

PESTICIDAL COMPOSITIONS

This application is a continuation-in-part of International Application Number PCT/EP2006/004094, filed on May 2, 2006, which claims priority to GB 0508993.3 filed May 3, 2005; and this application claims priority under 35 U.S.C. §119 to EP 06022767.5 filed Nov. 1, 2006, the contents of which are incorporated herein by reference.

The present invention relates to the use of a defined combination of pesticidal active ingredients, and compositions thereof, and methods for using such combinations in the control or prevention of pathogenic and/or pest damage, in particular in a plant propagation material and plant organs that grow at a later point in time by applying the compound on to the plant propagation material.

Certain combinations of active ingredients for controlling pathogens and pests are described in the literature. The biological properties of those known combinations are not entirely satisfactory in the areas of pathogenic control, phytotoxicity, and environmental and worker exposure, for example. In particular, in the instance a pathogen has become, or risks becoming resistant to the previously known combinations, improved methods of control or prevention are sought.

The protection of plant propagation materials (especially seeds) with active ingredients are target applications which partially address the need for a reduction of environmental and worker exposure when used alone or in conjunction with foliar or in-furrow active ingredient applications.

There is a continuing need to provide pesticidal combinations, which provide improved, for example, biological properties, for example, synergistic properties, especially for controlling pathogens.

That need is solved according to the invention by the provision of the present pesticidal combination. Accordingly, in a first aspect, the present invention provides a pesticidal combination comprising, preferably consisting essentially of, more preferably consisting of, at least three active ingredient components optionally together with one or more customary formulation auxiliaries, wherein component (I) is one or more of an -azole fungicide, component (II) is one or more of a phenylamide fungicide, component (III) is one or more of a strobilurin fungicide and/or one or more of a phenylpyrrole fungicide.

Examples of -azole fungicides are thiabendazole, oxpoconazole, ipconazole and prothioconazole; especially preferred are thiabendazole, ipconazole and prothioconazole.

Examples of phenylamide type fungicides include mefenoxam (metalaxyl-M), metalaxyl, benalaxyl, benalaxyl-M, oxadixyl and furalaxyl. Particularly preferred phenylamide type fungicides are mefenoxam (metalaxyl-M), metalaxyl, benalaxyl, benalaxyl-M.

Examples of strobilurin fungicides are azoxystrobin, picoxystrobin, metominostrobin, pyraclostrobin, famoxadone, fenamidone, fluoxastrobin, kresoxim-methyl, and trifloxystrobin. Particularly preferred strobilurin type fungicides are azoxystrobin, trifloxystrobin, fluoxastrobin, picoxystrobin, and kresoxim-methyl.

Examples of phenylpyrrole fungicides are fenpiclonil and fludioxonil; particularly preferred is fludioxonil.

Each of the combination demonstrates synergistic activity compared to activity of compounds alone.

In a second aspect, the present invention provides a method of controlling or preventing pathogenic damage or pest damage in a plant propagation material, a plant, parts of a plant and/or plant organs that grow at a later point in time, which comprises applying on the plant, part of the plant, or surroundings thereof, the combination as defined in the first aspect, in any desired sequence or simultaneously.

In a third aspect, the present invention provides a method of protecting a plant propagation material, a plant, parts of a plant and/or plant organs that grow at a later point in time against pathogenic damage or pest damage by applying to the plant, parts of plant, or their surroundings the combination, as defined in the first aspect, in any desired sequence or simultaneously.

The invention also relates to a plant propagation material treated with the combination defined in the first aspect.

Further, in an embodiment the present invention relates to a method which comprises (i) treating a plant propagation material, such as a seed, with a pesticidal combination as defined in the first aspect, and (ii) planting or sowing the treated propagation material, wherein the combination protects against pathogenic damage or pest damage of the treated plant propagation material, parts of plant and/or plant grown from the treated propagation material.

Also, in an embodiment the present invention relates to a method which comprises (i) treating a plant propagation material, such as a seed, with a pesticidal combination as defined in the first aspect, and (ii) planting or sowing the treated propagation material, and (iii) achieving protection against pathogenic damage or pest damage of the treated plant propagation material, parts of plant and/or plant grown from the treated propagation material.

In a preferred embodiment of any aspect of the invention, each combination is a composition comprising, preferably of, (I), (II) and (III), and optionally one or more customary formulation auxiliaries.

The components (I), (II) and (III) defined in the first aspect are active ingredients for use in the agrochemical industry (also known as pesticides). A description of their structure as well as other pesticides (e.g., fungicides, insecticides, nematicides) can be found in the e-Pesticide Manual, version 3.1, 13th Edition, Ed. CDC Tomlin, British Crop Protection Council, 2004-05.

Controlling, preventing or protecting and its inflections, within the context of the present invention, mean reducing any undesired effect, such as pathogenic, such as phytopathogenic, especially fungi, infestation or attack of, and pathogenic damage or pest damage on, a plant, part of the plant or plant propagation material to such a level that an improvement is demonstrated.

The pesticidal combinations according to the invention have very advantageous properties for protecting plants against (i) pathogenic, such as phytopathogenic, especially fungi, attack or infestation, which result in a disease and damage to the plant and/or (ii) pest attack or damage; particularly in instance of plants, the present invention can control or prevent pathogenic damage and/or pest damage on a seed, parts of plant and/or plant grown from the treated seed.

These properties are for example the synergistically enhanced action of combinations of compounds (I), (II) and (III), resulting in lower pathogenic damage and/or pest damage, lower rates of application, or a longer duration of action. In the instance of agriculture, the enhanced action is found to show an improvement in the growing characteristics of a plant by, for example, higher than expected control of the pathogenic infestation and/or pest damage.

The improvement in the growing (or growth) characteristics of a plant can manifest in a number of different ways, but ultimately it results in a better product of the plant. It can, for example, manifest in improving the yield and/or vigour of the plant or quality of the harvested product from the plant, which improvement may not be not connected to the control of diseases and/or pests.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

Accordingly, the present invention also provides a method of improving the growing characterictics of a plant, which comprises applying to the plant, and/or parts of plant, the combination, as defined in the first aspect, in any desired sequence or simultaneously.

In a preferred embodiment, combinations comprising (I) thiabendazole, (II) mefenoxam and (III) fludioxonil; (I) thiabendazole, (II) mefenoxam and (III) fludioxonil and azoxystrobin; (I) thiabendazole, (II) metalaxyl and (III) trifloxystrobin; (I) thiabendazole and ipconazole, (II) metalaxyl and (III) trifloxystrobin; (I) thiabendazole, (II) benalaxyl and (III) trifloxystrobin; (I) thiabendazole, (II) benalaxyl and (III) trifloxystrobin; (I) thiabendazole and ipconazole, (II) benalaxyl and (III) trifloxystrobin; (I) thiabendazole and prothioconazole, (II) metalaxyl and (III) trifloxystrobin; (I) thiabendazole and prothioconazole, (II) benalaxyl and (III) trifloxystrobin; (I) thiabendazole and prothioconazole, (II) metalaxyl and (III) fluoxstrobin; (I) thiabendazole and prothioconazole, (II) benalaxyl and (III) fluoxstrobin; (I) prothioconazole, (II) metalaxyl and (III) fluoxstrobin; (I) prothioconazole, (II) benalaxyl and (III) fluoxstrobin; (I) prothioconazole, (II) metalaxyl and (III) trifloxystrobin; (I) prothioconazole, (II) benalaxyl and (III) trifloxystrobin; are preferred.

In an embodiment, combinations comprising (I) thiabendazole, (II) mefenoxam and (III) azoxystrobin; (I) thiabendazole, (II) metalaxyl and (III) azoxystrobin; (I) thiabendazole, (II) benalaxyl-M and (III) azoxystrobin; (I) thiabendazole, (II) benalaxyl and (III) azoxystrobin; (I) thiabendazole and ipconazole, (II) metalaxyl and (III) azoxystrobin; (I) thiabendazole and ipconazole, (II) metalaxyl-M (mefenoxam) and (III) azoxystrobin; (I) thiabendazole and ipconazole, (II) benalaxyl-M and (III) azoxystrobin; (I) thia- bendazole and ipconazole, (II) benalaxyl and (III) azoxystrobin; (I) thiabendazole and prothioconazole, (II) metalaxyl and (III) azoxystrobin; (I) thiabendazole and prothioconazole, (II) metalaxyl-M and (III) azoxystrobin; (I) thiabendazole and prothioconazole, (II) benalaxyl and (III) azoxystrobin; (I) thiabendazole and prothioconazole, (II) benalaxyl-M and (III) azoxystrobin; (I) prothioconazole, (II) metalaxyl and (III) azoxystrobin; (I) prothioconazole, (II) metalaxyl-M and (III) azoxystrobin; (I) prothioconazole, (II) benalaxyl and (III) azoxystrobin; (I) prothioconazole, (II) benalaxyl-M and (III) azoxystrobin; are preferred.

The combination comprising (a) thiabendazole, metalaxyl, and pencycuron; (b) thiabendazole, ipconazole, metalaxyl, and pencycuron; or (c) thiabendazole, pencycuron and propamocarb is also found to control or prevent, in a further aspect of the invention, pathogenic damage in a plant propagation material, a plant, and/or plant organs that grow at a later point in time, when applying on the plant, part of the plant, or surroundings thereof, in any desired sequence or simultaneously.

Each of the combination of the invention can be used in the agricultural sector and related fields of use for controlling or preventing disease infestation and/or pest damage on plants.

Each of the combination according to the present invention is effective against phytopathogenic fungi, especially occurring in plants, including seedborne fungi and belong to the following classes: Ascomycetes (e.g. *Penicillium, Gaeumannomyces graminis*); *Basidiomycetes* (e.g. the genus *Hemileia, Rhizoctonia, Puccinia*); *Fungi imperfecti* (e.g. *Botrytis, Helminthosporium, Rhynchosporium, Fusarium, Septoria, Cercospora, Alternaria, Pyricularia* and *Pseudocercosporella herpotrichoides*); *Oomycetes* (e.g. *Phytophthora, Peronospora, Bremia, Pythium, Plasmopara*); *Zygomycetes* (e.g., *Rhizopus* spp.). A combination is especially effective against *Alternaria* spp., *Aspergillus* spp., *Claviceps purpurea, Cochliobolus* spp., *Colletotrichum* spp., *Diplodia maydis, Erysiphe graminis, Fusarium* spp. (such as *Fusarium culmorum, Fusarium oxysporium, Fusarium solani, Fusarium graminearum* and *Fusarium moniliforme*), *Gaeumannomyces graminis, Giberella fujikuroi, Giberella zeae, Helminthosporium graminearum, Monographella nivalis, Puccinia* spp., *Pyrenophora* spp. (such as *Pyrenophora graminea*), *Peronosclerospora* spp., *Peronspora* spp., *Phakopsora pachyrhizi, Phythium* spp., *Phoma* spp., *Phomopsis* spp., *Rhizoctonia solani, Septoria* spp., *Pseudocercosporella* spp., *Tilletia* spp., *Rhizopus* spp., *Typhula* spp., *Ustilago* spp., *Sphacelotheca* spp. (e.g. *Spacelotheca reilliani*), *Thanatephorus cucumeris*, and *Verticillium* spp.

The combinations of the present invention are particularly effective against fungal pathogens of the genus *Fusarium, Pythium* and/or *Rhizoctonia*.

The combinations of the invention can be formulated for a particular use. Preferably, the combination is formulated for protecting cultivated plants or their propagation materials. Accordingly, a combination of the invention can be applied to the plant in a conventional manner, such as foliar spray. Advantageously, the combinations are formulated for seed treatment applications for controlling or preventing damage by pests and/or pathogens, which are found in agriculture and forestry, and can particularly damage the plant in the early stages of its development.

Further, the present invention also envisages soil application of the combinations of the invention to control the soil-dwelling pests and/or soil-borne pathogens. Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods.

The benefit from the invention can also be achieved either by (i) treating plant propagation material with a combination or (ii) applying to the locus where control is desired, generally the planting site, the combination, or both (i) and (ii).

The term "plant propagation material" is understood to denote all the generative parts of the plant, such as seeds, which can be used for the multiplication of the latter and vegetative plant material such as cuttings and tubers (for example, potatoes). Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pathogenic and/or pest damage protection achieved by the application of the combination on to the plant propagation material. In an embodiment, certain parts of plant and certain plant organs that grow at later point in time can also be considered as plant propagation material, which can themselves be applied (or treated) with the combination; and consequently, the plant, further parts of the plant and further plant organs that develop from the treated parts of plant and treated plant organs can also benefit from the pathogenic and/or pest damage protection achieved by the application of the combination on to the certain parts of plant and certain plant organs.

Methods for applying or treating pesticidal active ingredients and mixtures thereof on to plant propagation material, especially seeds, are known in the art, and include dressing, coating, pelleting and soaking application methods of the propagation material.

The active ingredients can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In a preferred embodiment, the combination is applied or treated on to the plant propagation material by a method such that the germination is not induced; generally seed soaking induces germination because the moisture content of the resulting seed is too high. Accordingly, examples of suitable methods for applying (or treating) a plant propagation material, such as a seed, is seed dressing, seed coating or seed pelleting and alike.

It is preferred that the plant propagation material is a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the active ingredients and adherence thereof to the seeds is desired during propagation material treatment. Treatment could vary from a thin film (dressing) of the formulation containing the active ingredient(s) on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the active ingredients in the combination are adhered on to the seed and therefore available for pest and/or disease control.

The treated seeds can be stored, handled, sowed and tilled in the same manner as any other active ingredient treated seed.

The combination according to the present invention is suitable for plants of the crops: cereals (wheat, barley, rye, oats, corn, rice, sorghum, triticale and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, onions, tomatoes, potatoes, paprika); as well as ornamentals (flowers, shrubs, broad-leaved trees and evergreens, such as conifers). Especially suitable are wheat, barley, rye, oats, triticale, sorghum, corn, and soybean; each combination is advantageously preferred for the crops sorghum, corn and soybean.

Suitable target crops also include transgenic crop plants of the foregoing types. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The plant propagation material treated by a combination of the present invention are, therefore, resistant to disease and/or pest damage; accordingly, the present invention also provides a pathogenic and/or pest resistant plant propagation material which is treated with the combination and consequently at least the active ingredients thereof are adhered on the propagation material, such a seed.

The seed treatment combination and composition can also comprise or may be applied together and/or sequentially with further active compounds. These further compounds can be other pesticidal active ingredients, fertilizers or micronutrient donors or other preparations that influence plant growth, such as inoculants.

A single pesticidal active ingredient may have activity in more than area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

The combination of the present invention may be mixed with other pesticides, such as other fungicides, insecticides and nematicides.

Suitable examples include triazole derivatives, strobilurins, carbamate (including thiocarbamate), N-trihalomethylthio compounds (captan), substituted benzenes, carboxamides, and mixtures thereof; and neonicotinoids, carbamates, pyrethroids and mixtures thereof.

In a preferred embodiment, the combination comprising (I) thiabendazole, (II) mefenoxam and (III) fludioxonil, further comprises thiamethoxam; the combination comprising (I) thiabendazole and ipconazole, (II) metalaxyl and (III) trifloxystrobin, further comprises captan; the combination comprising (I) thiabendazole, (II) mefenoxam and (III) azoxystrobin and fludioxonil, further comprises thiamethoxam.

In the event a combination of the invention also includes a pesticide other than fungicide as compound (II) (such as abamectin, clothianidin, imidacloprid, thiamethoxam, tefluthrin, lambda-cyhalothrin) then the pesticide spectrum of the combination is broadened to include pest control, such as control of pests selected from Nematoda, Insecta and Arachnida. In that instance, the combination can also be applied on the pest to control or prevent pest damage and protect the desired material (e.g. plant and parts of plant) from pest damage. Examples of pests include:

from the order *Lepidoptera*, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia* spp., *Cryptophlebia leucotreta*, *Crysodeixis includens*, *Cydia* spp., *Diatraea* spp., *Diparopsis castanea*, *Earias* spp., *Elasmopalpus* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order *Coleoptera*, for example, *Agriotes* spp., *Anthonomus* spp., *Atomaria linearis*, *Ceutorhynchus* spp., *Chaetocnema tibialis*, *Cosmopolites* spp., *Curculio* spp., *Dermestes* spp., *Diabrotica* spp., *Epilachna* spp., *Eremnus* spp., *Gonocephalum* spp., *Heteronychus* spp., *Leptinotarsa decemlineata*, *Lissorhoptrus* spp., *Melolontha* spp., *Orycaephilus* spp., *Otiorhynchus* spp., *Phlyctinus* spp., *Phyllotreta* spp., *Popillia* spp., *Protostrophus* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp.;

from the order *Orthoptera*, for example, *Blatta* spp., *Blattella* spp., *Gryllotalpa* spp., *Leucophaea maderae*, *Locusta* spp., *Periplaneta* spp. and *Schistocerca* spp.;

from the order *Isoptera*, for example, *Reticulitermes* spp.;

from the order *Psocoptera*, for example, *Liposcelis* spp.;

from the order *Anoplura*, for example, *Haematopinus* spp., *Linognathus* spp., *Pediculus* spp., *Pemphigus* spp. and *Phylloxera* spp.;

from the order *Mallophaga*, for example, *Damalinea* spp. and *Trichodectes* spp.;

from the order *Thysanoptera*, for example, *Frankliniella* spp., *Hercinothrips* spp., *Taeniothrips* spp., *Thrips palmi*, *Thrips tabaci* and *Scirtothrips aurantii;* from the order *Heteroptera*, for example, *Dichelops melacanthus*, *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Triatoma* spp.;

from the order *Homoptera*, for example, *Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri;* from the order *Hymenoptera*, for example, *Acromyrmex*, *Athalia rosae*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.;

from the order *Diptera*, for example, *Antherigona soccata*, *Bibio hortulanus*, *Ceratitis* spp., *Chrysomyia* spp., *Culex* spp., *Cuterebra* spp., *Dacus* spp., *Delia* spp., *Drosophila melanogaster*, *Liriomyza* spp., *Melanagromyza* spp., *Orseolia* spp., *Oscinella frit*, *Pegomyia hyoscyami*, *Phorbia* spp., *Rhagoletis pomonella*, *Sciara* spp.;

from the order *Acarina*, for example, *Acarus siro*, *Aceria sheldoni*, *Aculus schlechtendali*, *Amblyomma* spp., *Argas* spp., *Brevipalpus* spp., *Bryobia praetiosa*, *Calipitrimerus* spp., *Chorioptes* spp., *Dermanyssus gallinae*, *Eotetranychus carpini*, *Eriophyes* spp., *Hyalomma* spp., *Olygonychus pratensis*, *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Tarsonemus* spp. and *Tetranychus* spp.; and from the class Nematoda, for example, the species of *Meloidogyne* spp. (for example, *Meloidogyne incoginita* and *Meloidogyne javanica*), *Heterodera* spp. (for example, *Heterodera glycines*, *Heterodera schachtii*, *Heterodera avenae* and *Heterodera trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and

*Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonlaimus* spp., *Criconemella* spp., *Criconemoides* spp. *Ditylenchus* spp., *Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Trichodorus* spp., *Quinisulcius* spp., *Scutellonema* spp., *Xiphinema* spp., and *Tylenchorhynchus* spp.

It is also found in a further aspect of the present invention that a combination comprising (i) thiabendazole and (ii) abamectin and/or a neonicotinoid pesticide, such as thiamethoxam, imidacloprid or clothianidin, is particularly well suited for control of pathogenic and pest damage, in particular in a corn, sugarbeet, sorghum or soybean crop. The combination is effective against nematode pests (such as any one of Lesion nematodes (*Pratylenchus* spp.) Sting nematodes (*Belonlaimus* spp.), root knot nematodes (*Meloidogyne* spp.), reniform nematodes (*Rotylenchulus* spp.), stubby root nematodes (*Trichodorus* spp.), cycst nematodes (*Heterodera* spp.), Lance nematodes (*Hoplolaimus* spp.)), in particular when the combination is applied onto a plant propagation material, such as a seed. A preferred combination comprises (i) thiabendazole and (ii) abamectin, and/or thiamethoxam.

The weight ratio of active ingredient compounds is selected as to give the desired, for example synergistic, action. In general, the weight ratio would vary depending on the specific active ingredient and how many active ingredients are present in the combination. Generally, in the event the combination consists of three active ingredients the weight ratio between any two ingredients, independently of each other, is from 100:1 to 1:100, preferably from 75:1 to 1:75, more preferably, 50:1 to 1.50, especially 25:1 to 1:25, advantageously 10:1 to 1:10, such as 5:1 to 1:5.

The rates of application (use) of the combination vary, for example, according to type of use, type of crop, the specific active ingredients in the combination, type of plant propagation material (if appropriate), but is such that the active ingredients in the combination is an effective amount to provide the desired enhanced action (such as disease or pest control) and can be determined by trials.

Generally for foliar or soil treatment, application rates can vary from 0.05 to 3 kg per hectare (g/ha) of active ingredients. In the instance of (I), (II) and (III) as defined herein, suitable application rates for foliar use are 50-1000, preferably 75-500, especially 100-300, g/ha of component (I); 50-1000, preferably 250-750 g/ha of component (I); 50-1000, preferably 75-500, especially 100-300, g/ha of component (III).

Generally for seed treatment, application rates can vary from 0.5 to 1000 g/100 kg of seeds of active ingredients. In the instance of (I), (II) and (III) as defined herein, suitable examples of application rates for seed treatment are tend to be 5-100, preferably 10-50, especially 12-25, g/100 kg of seeds of component (I); 0.5-10, preferably 0.75-7, especially 1-5, g/100 kg of seeds of component (II); 0.5-10, preferably 0.75-7, especially 1-5 g/100 kg of seeds of component (III).

In the event the combination comprises (I) thiabendazole, (II) mefenoxam and (III) fludioxonil, typical application rates for seed treatment, in particular on soybean, is 10-20 g of thiabendazole, 1-4 g of mefenoxam and 1-5 g of fludioxonil, each on g/100 kg of seeds basis.

In the event the combination comprises (I) thiabendazole, (II) mefenoxam and (III) fludioxonil and azoxystrobin, typical application rates for seed treatment, in particular on corn, is 15-25 g of thiabendazole, 1-4 g of mefenoxam, 1-5 g of fludioxonil and 0.5-2 g of azoxystrobin, each on g/100 kg of seeds basis.

In the event the combination comprises (I) thiabendazole, (II) mefenoxam and (III) fludioxonil, and thiamethoxam, typical application rates for seed treatment, in particular on soybean, is 10-20 g of thiabendazole, 1-4 g of mefenoxam, 1-5 g of fludioxonil, and 30-40 g of thiamethoxam, each on g/100 kg of seeds basis.

The compound, e.g., (I), (II) or (III), and any other pesticides, may be used either in pure form, i.e., as a solid active ingredient, for example, in a specific particle size, or preferably together with at least one of the auxiliary (also known as adjuvants) customary in formulation technology, such as extenders, e.g., solvents or solid carriers, or surface-active compounds (surfactants), in the form of a formulation, in the present invention. Generally, the compounds (I), (II) and (III) are in the form of a formulation composition with one or more of customary formulation auxiliaries.

Therefore, the combination of compounds, e.g., (I), (II) and (III), are normally used in the form of formulations. The compounds (I), (II) and (III) can be applied to the locus where control is desired either simultaneously or in succession at short interval, for example on the same day, if desired together with further carriers, surfactants or other application-promoting adjuvants customarily employed in formulation technology. In a preferred embodiment, (I), (II) and (III) are applied simultaneously.

In the event, for example, compounds (I), (II) and (III), are applied simultaneously in the present invention, they may be applied as a composition containing (I), (II) and (III), in which case each of (I), (II) and (III) can be obtained from a separate formulation source and mixed together (known as a tank-mix, ready-to-apply, spray broth, or slurry), optionally with other pesticides, or (I), (II) and (III) can be obtained as single formulation mixture source (known as a pre-mix, concentrate, formulated compound (or product)), and optionally mixed together with other pesticides.

In an embodiment, the combination of the present invention is applied as a composition. Accordingly, the present invention is a composition comprising, as active ingredients, (I), (II) and (III), and optionally other pesticides, and optionally one or more customary formulation auxiliaries; which may be in the form of a tank-mix or pre-mix composition In a preferred embodiment of the invention, the combination of (I) thiabendazole, (II) mefenoxam and (III) fludioxonil; (I) thiabendazole, (II) mefenoxam and (III) fludioxonil, and thiamethoxam; (I) thiabendazole, (II) mefenoxam and (III) azoxystrobin and fludioxonil; (I) thiabendazole, (II) mefenoxam and (III) azoxystrobin and fludioxonil, and thiamethoxam; thiabendazole and abamectin; thiabendazole and thiamethoxam; and thiabendazole, abamectin and thiamethoxam, are provided in the form of a pre-mix composition (or mixture).

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:

WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The formulations are prepared in known manner, e.g., by homogeneously mixing and/or grinding the active ingredients with extenders, e.g., solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g., for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g., especially dolomite or pulverized plant residues.

Depending upon the nature of the active ingredient compounds to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g., phosphatidylethanolamine, phosphatidylserine, phosphatidylglycerol and lysolecithin.

Generally, a tank-mix formulation for foliar or soil application comprises 0.1 to 20%, especially 0.1 to 15%, active ingredient compounds, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, active ingredient compounds, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, active ingredient compounds, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, active ingredient compounds, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The Examples which follow serve to illustrate the formulations suitable for compounds (I) and ((II), "active ingredient" denoting a combination of compound I and compound II in a specific mixing ratio.

FORMULATION EXAMPLES

| Wettable powders | a) | b) | c) |
|---|---|---|---|
| active ingredient [I:II = 1:6(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7–8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Dusts | a) | b) | c) |
|---|---|---|---|
| active ingredient [I:II = 1:6(a), 1:2(b), 1:10(c)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can be used for dry dressings for seed.

| Suspension concentrates | (a) | (b) |
|---|---|---|
| active ingredient (I:II = 1:1(a); 1:8(b)) | 5% | 30% |
| propylene glycol | 10% | 10% |
| Tristyrylphenol ethoxylates | 5% | 6% |
| sodium lignosulfonate | — | 10% |
| carboxymethylcellulose | — | 1% |
| silicone oil (in the form of a 75% emulsion in water) | 1% | 1% |
| Colour pigment | 5% | 5% |
| water | 74% | 37% |

The finely ground active ingredient is intimately mixed with the adjuvants, giving a suspension concentrate from which suspensions of any desired dilution can be obtained by dilution with water. Alternatively, a suspension of the active ingredients and auxiliaries (including water) is wet milled with a bead-mill to achieve a stable formulation and with the appropriate treatment characteristics.

Using such formulations either straight or diluted plant propagation material can be treated and protected against damage, for example, from pathogen(s), by spraying, pouring or immersing.

The active ingredient combinations according to the invention are distinguished by the fact that they are especially well tolerated by plants and are environmentally friendly.

Each active ingredient combination according to the invention is especially advantageous for the treatment of plant propagation material.

In a preferred embodiment, each of the combination of the present invention is a plant propagation material, preferably seed, treating composition.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples are given by way of illustration and not by way of limitation of the invention.

BIOLOGICAL EXAMPLES

Example 1

Activity of Mefenoxam, Fludioxinil and Thiabendazole Compositions Against *Fusarium* spp. on Corn Seeds 1. Agar test.

An agar test is performed to evaluate the effect of seed treatments with fludioxonil (2.5 g/100 kg seed)+mefenoxam (1.0 g/100 kg seed), thiabendazole at 10, 15 and 20 g/100 kg seed and the corresponding mixtures of all three components on seed health and viability of corn. Seed lots of corn cv. Magister, is infected artificially with either *F. proliferatum* or *F. subglutinans*, are used.

Czapek-Dox medium (OXOID) is prepared according to manufacturer's recipe: 45.4 g agar in 1 l aqua bidest., autoclaved for 15 min at 121° C., and is cooled down to 55° C. 15 ml medium is poured into each petridish (Ø 10 cm) and is allowed to cool.

10 seeds are placed on the surface of the agar. 5 replicates per treatment are done. Petridishes are placed in an incubator at 20° C. under NUV-light (12 h a day). The number of seeds where *Fusarium* spp. grew out on the agar is rated after an incubation period of 6 days.

2. Treatments

Mefenoxam (1.0 g ai/100 kg seed)+fludioxonil (2.5 g ai/100 kg seed).

Thiabendazole at 10, 15 and 20 g ai/100 kg seed.

Mefenoxam (1.0 g ai/100 kg seed)+fludioxonil (2.5 g ai/100 kg seed)+thiabendazole (at 10, 15 or 20 g ai/100 kg seed).

For combined treatments mefenoxam+fludioxonil are applied first on the seeds as a combined formulation and after drying the second application on the seeds with thiabendazole is performed.

3. Synergy

A synergistic effect exists, for example, whenever the action of an active ingredient combination is greater than the sum of the actions of the individual compounds.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient I using p ppm of active ingredient

Y=% action by active ingredient II using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

4. Results

TABLE 1

Activity of seed treatments on seed contamination and mycelium growth of *Fusarium* spp. on corn cv. Magister after 6 days.

| | FUSSUB | | | FUSPRO | | |
|---|---|---|---|---|---|---|
| Treatment | Contaminated Seeds | Mycelium Growth | Activity Observed | Contaminated Seeds | Mycelium Growth | Activity Observed |
| Check | 100 | 100 | 0 | 100 | 82 | 18 |
| Mefenoxam + Fludioxonil | 100 | 95 | 5 | 100 | 50 | 50 |

TABLE 1-continued

Activity of seed treatments on seed contamination and mycelium growth of *Fusarium* spp. on corn cv. Magister after 6 days.

| Treatment | FUSSUB | | | FUSPRO | | |
|---|---|---|---|---|---|---|
| | Contaminated Seeds | Mycelium Growth | Activity Observed | Contaminated Seeds | Mycelium Growth | Activity Observed |
| Thiabendazole (10 g) | 94 | 68 | 32 | 62 | 60 | 40 |
| Thiabendazole (15 g) | 100 | 40 | 60 | 44 | NA | NA |
| Thiabendazole (20 g) | 52 | 9 | 91 | 40 | NA | NA |
| Mefenoxam + Fludioxonil + Thiabendazole (10 g) | 98 | 46 | 54 | 60 | 8 | 92 |
| Mefenoxam + Fludioxonil + Thiabendazole (15 g) | 64 | 14 | 86 | 16 | 1.2 | 98.8 |
| Mefenoxam + Fludioxonil + Thiabendazole (20 g) | 30 | 3.6 | 96.4 | 0 | 0 | 100 |

Fusarium Subglutinans

The check shows that 100% infected seeds and 100% of the agar are overgrown by mycelium. Mefenoxam and fludioxonil (2.5 g ai and 1.0 g ai respectively) has no effect on number of infected seeds (100%) and on mycelium growth (95% of check). Only the highest rate of thiabendazole tested (20 g) shows a significant reduction of the number of infected seeds (9%). Mycelium growth is reduced by all thiabendazole treatments, showing a linear dose response. The combinations of mefenoxam and fludioxonil with thiabendazole at 10, 15 and 20 g reduce the number of infected seeds to 98%, 64% and 30%, respectively. Mycelium growth is reduced to 46, 14 and 4%, respectively, for the mix with 10, 15 and 20 g thiabendazole, respectively.

*Fusarium Proliferatum.*

The check shows 100% infected seeds and approximately 80% of the agar is overgrown by mycelium. Mefenoxam and fludioxonil (2.5 g ai/100 kg seed and 1.0 g ai/100 kg seed respectively) has no effect on number of infected seeds (100%) but reduces the mycelium growth to 50%. Thiabendazole at 10 g reduces both infected seeds and mycelium growth to ~60% of the check. Thiabendazole at 15 and 20 g reduces the number of infected seeds to 44 and 40%, respectively. The combinations of mefenoxam and fludioxonil with thiabendazole at 10, 15 and 20 g reduce the number of infected seeds to 60%, 16% and 0%, respectively. Mycelium growth is nearly completely inhibited by the mix with 10 and 15 g thiabendazole (8% and 1%, respectively) and complete inhibition is achieved by the mix with 20 g thiabendazole.

These results indicate that thiabendazole at the highest rate of 20 g/100 kg reduces the number of *Fusarium* infected seeds for both species. However, all combinations of mefenoxam, fludioxonil and thiabendazole reduce the count of *Fusarium* infected seeds, especially the mix with 20 g thiabendazole that exhibited excellent *Fusarium* control.

All mixtures of thiabendazole, mefenoxam and fludioxonil clearly outperform the most active solo ingredient of the mix at the given rate and most mixtures show synergistic interactions. Accordingly, the combinations of the invention show unexpected activity.

Example 2

Activity of Thiabendazole, Mefenoxam, Fludioxinil and Azoxystrobin Against *Fusarium Subglutinans* on Corn Seeds Seeds are prepared and inoculated as described in Example 1.

The pesticide containing seeds are treated with a combination of thiabendazole at 20 g, mefenoxam at 2 g, fludioxonil at 2.5 g and azoxystron at 1 g, each on a g/100 kg of seeds basis.

Table below illustrates the performance of the pesticide treatment compared to untreated seeds.

| | Emergence 9 DAS | Emergence 10 DAS | Final stand 21 DAS | Dry Weight in grams |
|---|---|---|---|---|
| UTC infected | 4.7 | 30.7 | 40.0 | 1.45 |
| Pesticide treated | 32.7 | 72.7 | 93.3 | 5.11 |

Example 3

Activity of Thiabendazole and Abamectin in Soybean

In a field having a heavy population of soybean cyst nematodes (*Heterodera glycines*), seeds are planted that have the following treatments:
 (a) fludioxonil (2.5 g ai/100 kg seed)+mefenoxam (3.75 g ai/100 kg seed)
 (b) fludioxonil (2.5 g ai/100 kg seed)+mefenoxam (3.75 g ai/100 kg seed), abamectin (0.25 mg ai/seed),
 (c) fludioxonil (2.5 g ai/100 kg seed)+mefenoxam (3.75 g ai/100 kg seed), abamectin (0.25 mg ai/seed)+thiabendazole (20 g ai/100 kg seed).

Table below shows the yield of the different treatments.

| | YIELD (Bushel/acre) | |
|---|---|---|
| (a) | 40 | C |
| (b) | 47 | B |
| (c) | 58 | A |

The results indicate that thiabendazole in combination with abamectin significantly increases soybean yields.

Example 4

Activity of Thiabendazole and Abamectin in Corn

In a field having a population of *Pratylenchus* spp. nematodes, corn seeds are planted that have the following treatments:

| treatment no. | active ingredient & rate |
|---|---|
| 1 | fludioxonil (3.5 g ai/100 kg seed), mefenoxam (1 g ai/100 kg seed), azoxystrobin (1 g ai/100 kg seed) and thiamethoxam (0.25 mg ai/seed) |
| 2 | treatment 1 and thiabendazole (0.05 mg ai/seed), |
| 3 | treatment 1 and abamectin (0.25 mg ai/seed) |
| 4 | treatment 1, thiabendazole (0.05 mg ai/seed) and abamectin (0.25 mg ai/seed) |

Table below shows the yield of the different treatments averaged over 6 trials each.

| treatment no. | Yield (bushels/acre) | % increase over treatment 1 | Expected according to Colby |
|---|---|---|---|
| 1 | 123.65 | — | — |
| 2 | 137.37 | 11.1% | — |
| 3 | 124.36 | 0.6% | — |
| 4 | 145.25 | 17.5% | 11.6% |

Example 5

Activity of Thiabendazole and Abamectin in Sugarbeet

Sugarbeet seeds are treated with treatments 1 to 4 (see Table below) and are planted in small plastic tubes containing steamed natural soil with low organic matter. After 2 weeks the plants are inoculated with 500 larvae/plant of *Heterodera schactii* the inoculation is repeated after one more week with 500 larvae. Each treatment is replicated 4 times.

| treatment no. | active ingredient & rate |
|---|---|
| 1 Check | fludioxonil (6 g ai/unit), mefenoxam (0.5 g ai/unit) |
| 2 | treatment 1 and thiabendazole (0.2 g ai/unit), |
| 3 | treatment 1 and abamectin (30 g ai/unit) |
| 4 | treatment 1, thiabendazole (0.2 g ai/unit) and abamectin (30 g ai/unit) |

1 unit = 100 000 seeds

When plants are 6 week old the assessment of number of cysts/plant is carried out. The soil is washed away very carefully from the roots and the cysts are assessed under the microscope based on:

0-9 cysts/plant gives index 9, 10-29 cysts/plant gives index 7, 30-49 cysts/plant gives index 5, 60-69 cysts/plant gives index 3 and >70 cysts/plant gives index 1.

The Disease Index is calculated: $DI = n*1 + n*3 + n*5 + n*7 + n*9/\text{Total number of plants}$. Table below illustrates Disease index from 1-9, with 1 indicating many cysts and 9 indicating perfect protection of the plant root against cyst nematode.

| Replicate | Treatment | | | |
|---|---|---|---|---|
| | 1 Check | 2 | 3 | 4 |
| 1 | 3.75 | 3.46 | 4.43 | 7.71 |
| 2 | 3.29 | 1.86 | 5.36 | 6.69 |
| 3 | 1.2 | 1 | 3.15 | 7.6 |
| 4 | 4.78 | 6.4 | 5.29 | 4 |

Table below shows the synergistic response of abamectin and thiabendazole:

| treatment no. | Protection level (averaged) | % increase over treatment 1 | Expected according to Colby |
|---|---|---|---|
| 1 Check | 3.2 | — | — |
| 2 | 3.2 | 0 | — |
| 3 | 4.6 | 58.3 | — |
| 4 | 6.5 | 103.1 | 58.3 |

The invention claimed is:

1. A synergistic pesticidal combination comprising at least three active ingredient components optionally together with one or more customary formulation auxiliaries, wherein component (I) is thiabendazole, component (II) is mefenoxam, component (III) is fludioxonil; and wherein the pesticidal combination displays synergy when applied to corn seeds at a rate of 15 mg or less of thiabendazole per 100 kg corn seed.

2. The combination according to claim 1, wherein the combination further comprises one or more other insecticides and/or nematicides.

3. The combination according to claim 1 wherein the combination further comprises thiamethoxam.

4. The combination according to claim 1, in the form of a pesticidal composition for treating plant propagation material.

5. A method of controlling or preventing pathogenic damage or pest damage in a plant propagation material, a plant, parts of a plant and/or plant organs that grow at a later point in time, which comprises applying on the plant propagation material, the plant, part of the plant, or surroundings thereof, synergistically effective amounts of (I) thiabendazole, wherein the rate of application of thiabendazole is 15 mg or less per 100 kg of plant propagation material (II) mefenoxam, and (III) fludioxonil.

6. Plant propagation material treated with the combination defined in claim 1.

7. The method according to claim 5, further comprising thiamethoxam.

8. The method according to claim 5, further comprising azoxystrobin.

9. The method according to claim 8, further comprising thiamethoxam.

10. Plant propagation material treated with the combination according to claim 2.

11. Plant propagation material treated with the combination according to claim 3.

* * * * *